United States Patent [19]

Potter et al.

[11] Patent Number: 4,867,154
[45] Date of Patent: Sep. 19, 1989

[54] ENDOTRACHEAL TUBE STABILIZING DEVICES

[75] Inventors: Anthony B. Potter, Crozet; John K. Wilson, Charlottesville, both of Va.; Kirk Quackenbush, Broomfield, Colo.; E. Jane Dwyer, Howardsville, Va.

[73] Assignee: The University of Virginia Alumni Patents Foundation, Charlottesville, Va.

[21] Appl. No.: 105,539
[22] Filed: Oct. 8, 1987
[51] Int. Cl.$^4$ ............................................. A61M 16/00
[52] U.S. Cl. ........................ 128/207.17; 128/DIG. 26; 604/180
[58] Field of Search ............ 128/207.14, 207.17, 128/DIG. 26; 604/174, 178, 179, 180, 116

[56] References Cited

U.S. PATENT DOCUMENTS

| | | | |
|---|---|---|---|
| 3,338,538 | 8/1967 | Roche | 128/DIG. 26 |
| 3,428,046 | 2/1969 | Remer et al. | 128/344 |
| 3,946,742 | 3/1976 | Eross | 128/207.17 |
| 3,990,454 | 11/1976 | Schlesinger | 604/180 |
| 4,089,337 | 5/1978 | Kronner | 604/178 |
| 4,270,529 | 6/1981 | Muto | 128/207.17 |
| 4,329,984 | 5/1982 | Kervin | 128/207.14 |
| 4,392,857 | 7/1983 | Beran | 604/179 |
| 4,548,200 | 10/1985 | Wapner | 128/207.17 |
| 4,683,882 | 8/1987 | Laird | 128/207.17 |
| 4,700,432 | 10/1987 | Fennell | 604/179 |
| 4,702,736 | 10/1987 | Kalt et al. | 128/DIG. 26 |

Primary Examiner—Max Hindenburg
Assistant Examiner—John P. Lacyk
Attorney, Agent, or Firm—James Creighton Wray

[57] ABSTRACT

Frames for endotracheal tubes are disclosed. One device consists of a U-shaped band made of semirigid plastic material which passes over the patient's lower face and which attaches at either end to the patient's cheeks and/or temples. The part of the band which passes over the area of the mouth, for orally intubated patients, or over the nose, for nasally intubated patients, has a clamping device which holds the endotracheal tube securely but which can be applied and released quickly and easily. Wire frames are also provided with similar clamps. The clamp consists of a longitudinal channel which may have one or more short spikes embedded in it and into which the tube is placed. A wide strap then wraps around the tube and locks in place thereby holding the tube tightly in the channel.

12 Claims, 2 Drawing Sheets

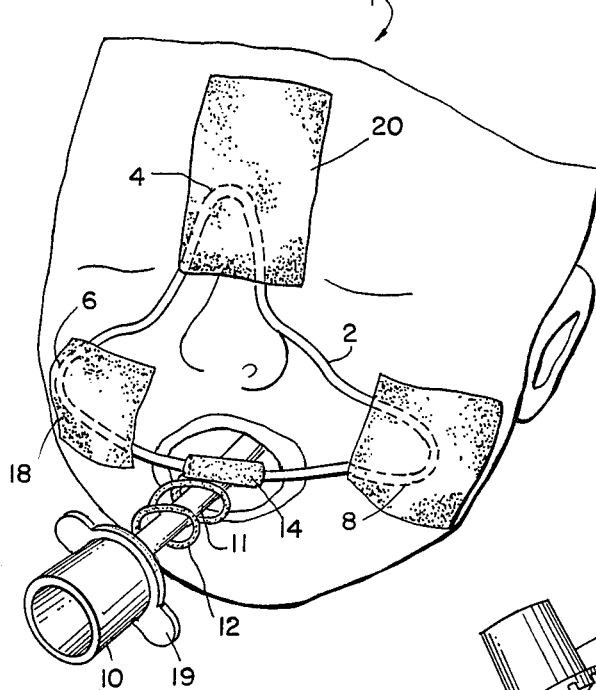
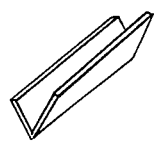
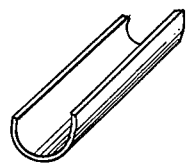
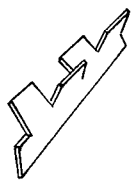
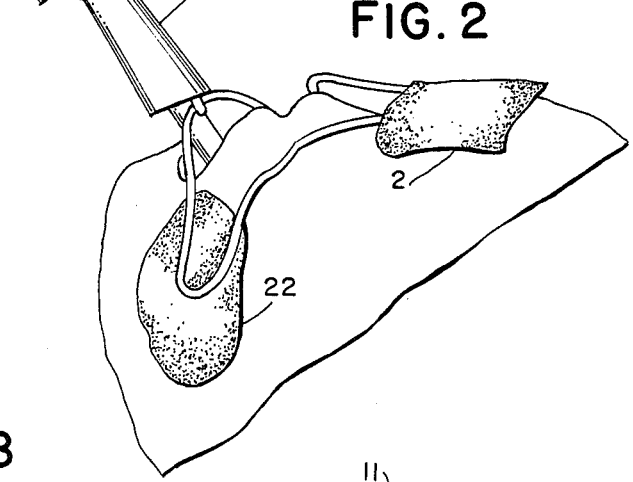
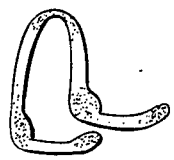
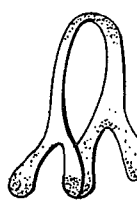
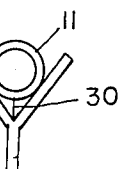
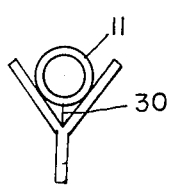
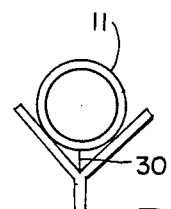

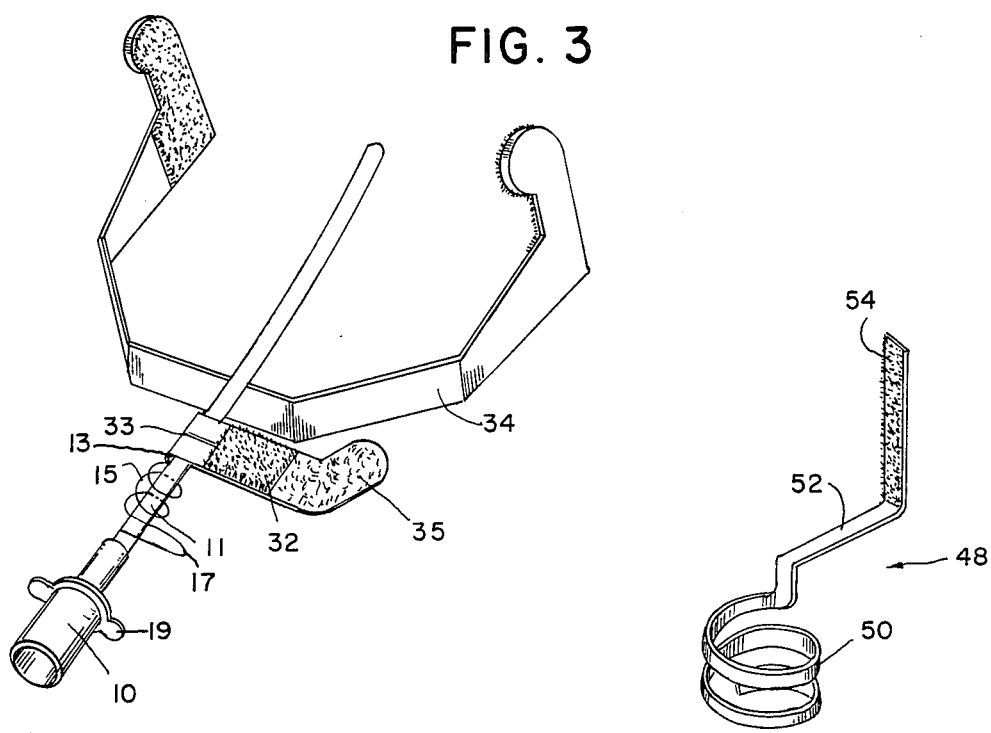
FIG. 3
FIG. 13
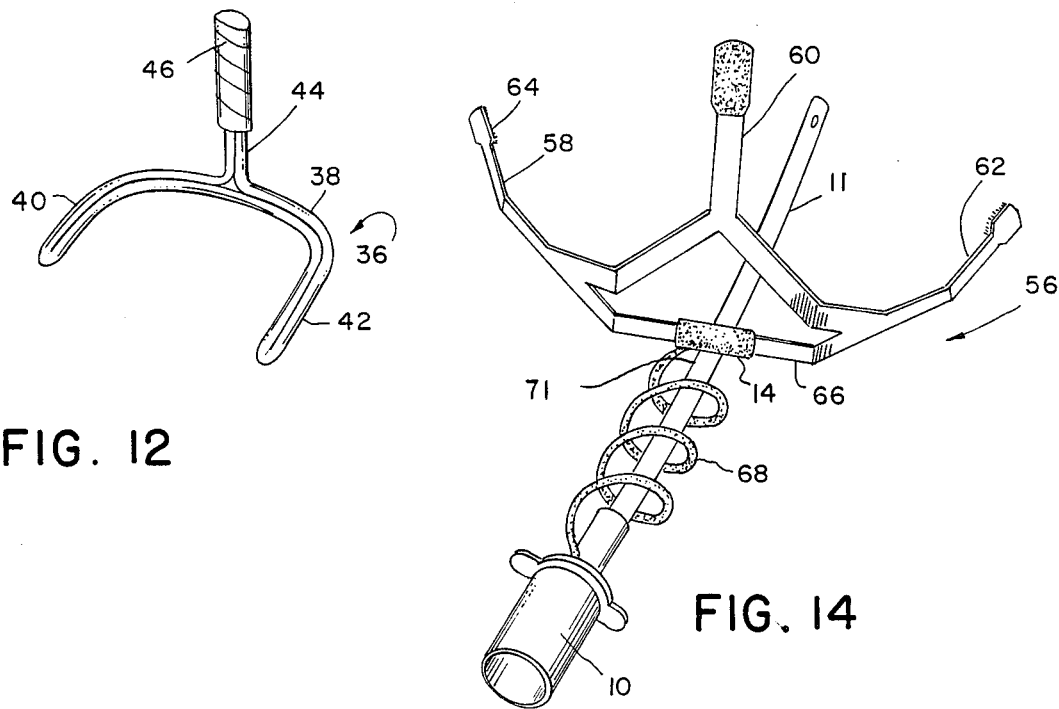
FIG. 12
FIG. 14

ENDOTRACHEAL TUBE STABILIZING DEVICES

BACKGROUND OF THE INVENTION

A currently used method of stabilizing endotracheal (E.T.) tubes is the popular method of taping the tube to the patient's mouth with surgical adhesive tape. However, this method has many problems, among them:

(1) Taping requires special skill and care, and if it is executed incorrectly the tube can still move in and out of the patient's mouth enough to cause significant irritation of the trachea.

(2) Saliva collects on the tape, and the tape in turn loses its adhesive efficacy, presenting the possibility of tube migration or accidental extubation. This problem also promotes biological contamination.

(3) Periodic replacement of the adhesive tape (due to problem No. 2 above) causes irritation of the patient's skin, especially in those patients requiring long term intubation. Long term intubation is not uncommon in neonatal and pediatric intensive care units.

(4) Any slight adjustments to the tube's position require removal of the tape and then retaping.

(5) Access to the mouth for suctioning etc. is made difficult by the presence of the tape.

There have been many attempts to provide stabilization for endotracheal tubes. Often the prior devices fail to address the problems associated with the taping method in a way that is suitable for neonatal and pediatric applications. That is why the taping method is still so widely used. Some devices, such as those shown in U.S. Pat. Nos. 4,191,180, 4,331,143 and 4,537,192, employ straps which pass behind the head and/or neck. While the use of straps provides more rigid tube support, straps are undesirable on infants whose heads are growing rapidly, especially when long term intubation is involved. Also, the straps can become entangled in the patient's bedsheets. Other devices, such as those shown in U.S. Pat. Nos. 3,993,081 and 3,713,448, are overly complicated to apply, especially when exact positioning of the tube within the tracea is critical, as is the case with small babies. Still other devices, such as what is shown in U.S. Pat. No. 4,329,984, are no better than the taping method, in that they still require taping in the area of the mouth, resulting in restricted access to the mouth and the attendant problems with saliva. Some proposed solutions (patents 4,331,143 and 4,537,192) cover vital areas of the patient's face such as the nose, mouth, and eyes, restricting access. The devices described in patents 4,331,143 and 4,537,192 do not address the means of attachment of the tube to the stabilization device in a credible manner. Mere "frictional restraint" is not a sufficiently reliable means of holding endotracheal tubes in the clinical setting.

SUMMARY OF THE INVENTION

The present invention solves the aforementioned problems asssociated with the prior art by providing endotracheal tube supports that are effective, easy to install and easy to adjust. The frames disclosed herein are provided with a unique attachment means which distributes the gripping force applied to the endotracheal tube so as to provide adequate support and ease of adjustment simultaneously.

The frames are preferably made of bendable material, such as wire or plastic, which allows the physician to make adjustments in the shape of the frame to accommodate variations in patient size and head shapes.

In one embodiment of the invention, the frame is made of wire and is shaped to include three attachment points which actually correspond to the three corners of a triangularly shaped member. The three corners are rounded and conform to the shape of an infant's head by having one corner attached to the forehead, this corner corresponding to an apex of the triangle, and the other two corners being attachable to the zygoma region, these two corners corresponding to the base of the triangle. The wire is shaped to define a nose piece so that opposite ends of the wire terminate at the nose piece.

The frame is taped to three stomahesive patches. "Stomahesive" is a trademark of Squibb and consists of a thin wafer of cellulose material having an adhesive surface and a peel-off wax paper covering for the adhesive which is removed prior to use. One patch is placed over each zygoma and a third on the forehead. After placement of the corners of the frame over the stomahesive patches, tape is placed over the stomahesive patch in order to bind the corners to the stomahesive patch. In this embodiment, the endotracheal tube itself is secured to the frame by a single piece of tape wrapped two or three times around a nose piece extending upwardly from the frame in the region of the mouth and nose. This tape should be as water repellent as possible so that secretions do not loosen it from the frame.

In order to install the device, observations must be made as to the shape and size of the patient's head. Based on these observations, a properly sized frame can be adjusted by making bends where necessary in order to derive an optimal shape. The adjustments should leave the frame balanced such that all three corners rest flatly against the patient's face, without having any other part of the frame touch the face.

Once the frame is fitted to the individual requirements of the patient, taping of the frame to the head can proceed.

First, three stomahesive patches are cut, with preferably two smaller ovals provided for the zygoma and a more narrow oval for the forehead. Use of benzoin on the skin to apply the patches is preferable.

After intubation, the frame is applied to the stomahesive patches and held in place with tape. Once all three corners are secure, the endotracheal tube is taped to the frame's nose piece. The nose piece can be radially outwardly extending support which provides rigidity of the tube over a substantial length.

The frame itself is substantially planar except for the zygoma corners which bend slightly to conform to the shape of the patient's head. However, the frame remains close to the patient's face to minimize risk of bumping.

Part of the invention lies in the ease with which the device can be attached. The attachment means includes tape which attaches the frame to "off-the-shelf" stomahesive pads. This substantially reduces the cost and increases the ease with which the device can be attached. The stomahesive pads, as is generally known by those of ordinary skill in the art, have adhesive between the face and the pad.

The use of tape to secure the tube to the frame is likewise effective and inexpensive. Other types of attachment means may be used, such as latches that use channels and spring biasing means to hold the tube within the channel. Spring loaded latches may be used, such as those used in broom holders or test tube holders.

Latches without springs, such as those that hold pencils in drafting compasses, could also be used. Rubber or small barbs on the inside of the latch could be used to prevent migration of the endotracheal tube.

The tube support of the present invention secures and supports the endotracheal tube along its length rather than restraining it at a single point. By so doing, the tube can be secured down to the infant's lip and does not need to be taped to the face or lip as is required in the prior art.

Another advantage to the present invention lies in the ease with which the device can be adjusted with respect to the placement of the tube in the patient's airway. Accurate adjustment of endotracheal tube placement is possible when using the tube support latch. With the latch, or even with the tape, the tube can be untaped or unlatched and moved axially, and then relatched or retaped in the desired position.

The advantages to the aforementioned embodiment include that it is disposable, easy to fabricate from plastic or metal, quickly molded to "glove fit" individual facial shapes, and more attractive to parents and comfortable for the infant. The device also prevents skin damage since no tape is attached to the child. Instead, the tape is attached to the stomahesive.

Another advantage is that positive stabilization of the endotracheal tube prevents damage to the airway of both long and short term intubations.

The device provides a stable tube, making suctioning and tube adjustment easier. Because of the attachment means, quick release is allowed for improved emergency airway access.

The endotracheal tube stabilizers herein described have the following advantages: (1) They do not use straps around the head. (2) They do not restrict access to the nose, mouth, or eyes, and (3) They do not rely upon taping in the area of the mouth. Furthermore, because of the quick release tube clamp, the frame can be applied quickly and easily after intubation without disturbing the tube placement. Conversely, it can be removed quickly in the case of an emergency. These considerations render it particularly suitable for, but not limited to, neonatal and pediatric applications.

A band which passes over the mouth of the patient is provided in each embodiment. The precise shape of the device may vary. For example, the ends of the band may be "L" shaped or "Y" shaped or simply wider to increase the area of attachment to the patient's skin, thereby increasing the stability of the device when attached. The material used in construction should be pliable and strong enough to permit the device to be "bent to fit" the individual patient. Polycarbonate plastic is well suited for this. The clamp which holds the tube consists of a channel which protrudes orthogonally from the plane of the patient's face. This channel may be "C" shaped or V shaped in cross section or may consist of "fingers" bent to alternate directions. This channel has one or more spikes embedded along its length. These spikes are of such a length as to barely stick into the walls of endotracheal tubes of various sizes when they are laid along the channel. This prevents the tube from slipping in the channel even in the presence of saliva. A strap which is permanently attached to one side of the channel wraps around the tube after it is placed in the channel. The free end of the strap can be held tightly in place with VELCRO, or any other means which permits incremental adjustments to accommodate different tube diameters. Endotracheal tube sizes vary from 2.5 mm to over 4.0 mm diameter.

One embodiment of the invention uses a transparent material whenever possible to facilitate the close monitoring of the patient's face and the tube's position. This also results in an appearance much improved over that of tape over the mouth, reducing the distress of the patient's family. A marker line indelibly imprinted on the clear strap which holds the tube in the channel further facilitates the documentation and monitoring of the exact position of the tube (the tubes have lettering and other marks along them). The preferred embodiment passes over the patient's lower lip for orally intubated patients or maximize the clearance from the nasal area, although the frame could also be used for nasally intubated patients. An optional alternative flexible coil support, whose distance from the mouth can be adjusted by bending it, is attached above the clamping device to reduce the risk of kinking the tube. The tube is introduced into the coil support by winding the coil around it several times. Another coil is rubber coated to prevent migration of the tube as well as to prevent kinking. To prevent possible migration of the tube due to repeated flexing of this rubber coil, one or more spikes are located at the base of the coil.

The preferred system of attachment of the frame to the patient's skin for the band frame is described as follows: Self adhesive VELCRO pads are stuck to both ends of the frame at the points of contact with the patient's skin. Matching VELCRO pads are stuck to pieces of surgical adhesive (flesh colored cloth bandages are ideal). The specially prepared pads are stuck to the patient's skin at the points of contact with the frame after first preparing the skin with tincture of benzoin. Application of the frame then requires merely pressing the frame in place on the patient's face. The exact point of contact on the patient's face can vary from the cheek back to the ear, and thus one size of frame can fit a wide range of different sized faces. However, different sized frames are necessitated to fit the entire range of babies from early premature through childhood.

The systems of attachment discussed above allow for quick removal of the frame in case of emergency. The VELCRO patches would be left attached to the patient until the emergency passes and the frame and tube could be re-applied. The same methodology would hold for the stomahesive patches. Removal of the frame is much quicker than the prior art and no adhesives are hastily pulled from the patient's face.

BRIEF DESCRIPTION OF THE DRAWINGS

FIG. 1 is a perspective view of one embodiment of the frame with one embodiment of the attachment means for attaching the frame to the face and another attachment means for attaching the tube to the frame.

FIG. 2 is another perspective view of the embodiment of the frame shown in FIG. 1 from an opposite angle, showing one corner of the frame untaped and showing another attachment means for attaching the tube to the frame.

FIG. 3 is a detail side elevation of another embodiment of the frame with another embodiment of attachment means for attaching the tube to the frame.

FIGS. 4, 5 and 6 are alternative perspective views of the tube support which may be used in the embodiment of FIG. 3 or in the embodiment of FIG. 1.

FIGS. 7, 8 and 9 are alternative perspective views showing the overall shape of the frame depicted in FIG. 3.

FIGS. 10 and 11 are cross-sectional views showing how a barb in the channel can accommodate endotrachael tubes of varying diameter.

FIGS. 12–14 are perspective views of other embodiments of the invention.

DETAILED DESCRIPTION OF THE DRAWINGS

Referring to FIG. 1, a frame is generally referred to by the numeral 1. The frame has an endless loop wire 1 that is bent into a triangular shape with rounded corners 4, 6 and 8. At an area of the frame near the nose and mouth, means are provided for securing an endotracheal tube in an intubated position. The means includes an adapter 10 which is part of an endotracheal tube. The tube and adapter are standard equipment.

In the normal course of events, the adapter 10 is removed after the tube has been inserted in the patient's airway. The flexible part of the endotracheal tube is then cut so that it extends slightly beyond the peak of the nose piece/latch on the frame. The adapter 10 is then re-inserted into the flexible endotracheal tube and secured by the latch 19.

The support 12 is intended to have a substantial length in order to support the tube over the substantial length between the patient's lip and the adapter. Once the tube is put in place, tape 14 is wrapped around the support 12 along the longitudinal portion thereof so that the tube is held over a substantial length. In FIG. 1, the frame is shown attached to an infant's face with two pieces of tape 18 disposed over the zygoma region and one piece of tape 20 over the forehead.

As shown in FIG. 2, the pieces of tape are adhered to a stomahesive pad 22 and not to the infant's skin. Preferably, the stomahesive pads 22 are oval shaped.

The frame of FIG. 1 may include any of the tube attachment means previously described in the specification. For instance, the support 12 may be provided with a latch which includes a substantially cylindrically shaped channel and a lever actuated leaf spring, such as those commonly found on drafting compasses to hold pencils in place.

Variations in the shape of the frame are shown in FIGS. 7, 8 and 9. In each of these embodiments, a band 34, as shown in FIG. 3, as intended to pass above the mouth and nose region of the patient. Each of the embodiments of FIGS. 7, 8 and 9 have end regions of the band which extend radially outwardly to provide points of attachment using the previously described VELCRO pads and tape. The embodiments of FIGS. 7 and 8 have four points of attachment. In FIG. 7, these points include end portions of the band and end portions of the radially outwardly extending arms. FIG. 7 of the application may also be attached at two points. This would be along the length of both arms of the frame where it rests on the patient's face. See, for instance, FIG. 3. In FIG. 8, the points of attachment are the forked ends of the band.

In FIG. 3, a preferred attachment means for attaching the endotracheal tube is illustrated. A channel 13 is connected to the band 34 and extends radially outwardly from the band. The channel and latch end at the face of the band 34. Variations of the channel 13 are shown in FIGS. 4, 5 and 6 wherein the channel can be V shaped, C shaped, or Y shaped. In any of the channels shown in FIGS. 4, 5 and 6, a barb or barbs 30, as shown in FIGS. 10 and 11, are preferably provided in the deepest part of the channel so as to grab the tube 11 and help prevent incidental sliding of the tube within the channel. It can be seen by comparing FIGS. 10 and 11 that endotracheal tubes 11 of varying diameter can be accommodated in the same size channel. For the smaller tube 11 of FIG. 10, the barb would stick further into the wall of the tube because the tube would fit deeper into the channel.

Referring back to FIG. 3, one means of attaching the tube and fixing it in the channel 13 is to use a clear strap 32. A marker line 33 indelibly printed on the clear strap which holds the tube in the channel facilitates the documentation and monitoring of the exact position of the tube. In this embodiment, the tubes would have lettering or other graduation marks which could be aligned with the marker line 33. The graduation marks may include numbers which correspond to millimeters of length or other suitable measuring lengths.

Also shown in FIG. 3 is a coiled support 15 which may be bent at a bendable arm portion 17 to move the coiled portion up and down. By moving the coil up, the risk of kinking of the tube can be reduced.

Again referring to FIG. 3, the clear strap 32 may simply wrap around the channel 13 and the tube or it may wrap around the channel and tube and attach to a backing plate 35. Backing plate 35 provides sufficient surface area to allow strap 32 to securely hold the tube. As shown in FIG. 3 the backing plate may be covered with Velcro to allow attachment of strap 32 to its surface. The backing plate 35 may be a solid plate or a flexible sheet. In a variation on the invention, the strap 32 may include micro-hook and micro-loop complementary fasteners on opposite surfaces so that the strap is wrapped around the tube and attached to itself to secure the tube.

In another variation on the invention, the channel 13 shown in FIG. 3 could be provided with a latch instead of tape or straps. The latch would be preferably used with a C-shaped channel, such as what is illustrated in FIGS. 3 and 5. In such embodiment, the open portion of the C-shaped channel would be provided with a latch mechanism which grips the tube and ungrips the tube, depending on whether the latch is latched or unlatched.

The FIGS. 1 and 2 embodiment is a simple wire frame in a triangular shape which is attached by the stomahesive pads and tape. A similar result can be achieved by forming a C-shaped frame from wire as shown in FIG. 12. This frame is advantageous because of its simplicity. A single wire may be bent to form a frame 36 having a band 38 terminating in opposite attachment ends 40, 42. A nose piece 44 is formed by ends of the wire wrapped in tape 46.

A plastic frame may be used instead of wire. The embodiment of FIG. 3 is formed from plastic materials, such as polycarbonate. This preferred embodiment uses VELCRO-type complementary fasteners for attaching the device to a patient's face and for holding the tube in place.

FIG. 13 illustrates a small, coiled plastic piece 48 with VELCRO strip 54 that fits onto the nose piece of FIG. 3 to provide additional support for the tube. This would be an optional piece that could be used if the flexible part of the endotracheal tube extended beyond the latch/nose piece. This would most likely be the case in those situations where the endotracheal tube was not cut to the proper length after insertion. The coil 50 and support 52 could also be designed as an integral part of the frame that could be snapped off if not needed. Tubes are typically cut shorter if they extend beyond the latch. Because of this, the above mentioned coil is not always necessary and is an optional rather than required component.

Another plastic frame embodiment is shown in FIG. 14. The frame 56 includes support legs 58, 60, 62, each having fastener means 64 on end portions, such as VELCRO-type complementary fastener means in which the complementary fastener is attached to the patient's face.

The frame further includes band 66 passing over the nose/mouth region of the patient. A coiled wire 68 is coated with frictional plastic which is capable of gripping tube 11 for holding the position of the tube and also for preventing kinking. Once the tube 11 is in place, tape 14 is wrapped around the coil wire 68 along the longitudinal portion thereof so that the tube is held over a substantial length. A spike 71 prevents possible gradual migration of the tube due to repeated flexing of the coil. A moldable frictional plastic or other natural or synthetic material may be used without wire so long as the material is semirigid or bendable.

While the present invention has been described with reference to specific examples, drawings and embodiments, variations may be made without departing from the invention.

We claim:

1. An endotracheal tube stabilizer comprising:
   a band-shaped frame, wherein the frame comprises an extension band for extension in front of the mouth region of the patient, wherein the band has opposite end portions adapted to be connectable to opposite side portions of the patient's face:
   means for attaching the frame to a patient's face, wherein the means for attaching the frame comprises at least two stomahesive pads adapted to be adhesively connected to the patient's face, wherein opposite side portions of the frame are overlaid on an upper surface of the stomahesive pads, and tape overlies the stomahesive pads and the opposite side portions of the frame for holding the frame to these stomahesive pads;
   a support having distal and proximal ends, wherein the proximal end of the support is connected to the frame and the support extends radially outward from the frame; and
   means for securing an endotracheal tube to the support.

2. The stabilizer of claim 1 wherein the means for securing the endotracheal tube to the support comprises tape which is wrapped around the tube and the support.

3. The stabilizer of claim 1 wherein the opposite end portions comprise band extensions extending substantially perpendicularly to the band.

4. The stabilizer of claim 1 wherein the end portions comprise rounded ends.

5. The apparatus of claim 1 wherein the support comprises a channel receiving the endotracheal tube.

6. An endotracheal tube stabilizer comprising, a band shaped frame,
   means for positioning the frame close to a patient's face,
   means for attaching the frame to a patient's face at points of attachment substantially far away from the patient's mouth and nose,
   a support connected to the frame at an area of the mouth and nose of the patient, wherein the support extends radially outwardly from the frame, and
   means for securing an endotracheal tube to the support wherein the support comprises a channel receiving the endotracheal tube wherein the means for securing the endotracheal tube comprises a transparent strap connected to one side of the channel, wherein the strap wraps around the endotracheal tube.

7. The stabilizer of claim 6 wherein the transparent strap is provided with a marker line, whereby the position of the tube is determined by alignment of the marker line with graduated markers.

8. The apparatus of claim 1 further comprising, a coil, connected to a distal end of a support and being wrapped around the endotracheal tube, wherein moving the coil up the tube prevents kinking.

9. The apparatus of claim 5 wherein the means for securing the endotracheal tube to a channel comprises two straps having complementary microhook and microloop fastener means provided thereon.

10. The stabilizer of claim 9 wherein the channel is provided with at least one barb in a deepest part of the channel wherein the barb prevents incidental sliding of the tube.

11. The stabilizer of claim 10 wherein the channel is C shaped.

12. The stabilizer of claim 1 wherein the means for securing the endotracheal tube to the support comprises latch means, wherein the latch means has a substantially cylindrically shaped channel for receiving the endotracheal tube at an end portion thereof and grip means movable in a radially inward direction for gripping the endotracheal tube.

* * * * *